(12) United States Patent
Cheng et al.

(10) Patent No.: US 6,180,836 B1
(45) Date of Patent: Jan. 30, 2001

(54) PREPARATION OF PHENOL VIA ONE-STEP HYDROXYLATION OF BENZENE CATALYZED BY COPPER-CONTAINING MOLECULAR SIEVE

(75) Inventors: Soofin Cheng, Taipei; Berryinne Chou, Kaohsiung, both of (TW)

(73) Assignee: National Science Council of Republic of China, Taipei (TW)

( * ) Notice: Under 35 U.S.C. 154(b), the term of this patent shall be extended for 0 days.

(21) Appl. No.: 09/375,447

(22) Filed: Aug. 17, 1999

(51) Int. Cl.$^7$ ...................................................... C07L 37/00
(52) U.S. Cl. ................................................................. 568/803
(58) Field of Search ................................................ 568/803

(56) References Cited

FOREIGN PATENT DOCUMENTS 58-96033A * 6/1983 (JP) .

* cited by examiner

*Primary Examiner*—Michael L. Shippen
(74) *Attorney, Agent, or Firm*—Bacon & Thomas

(57) ABSTRACT

The invention relates to a novel one-step process for preparation of phenol by oxidation of benzene with hydrogen peroxide catalyzed by molecular sieves doped with copper ions. With proper solvent, a phenol yield around 15–35%, selectivity close to 100% and phenol/Cu TON around 100 could be achieved. These results show that the inventive process is of great economical value for further development in large scale production of phenol.

18 Claims, 3 Drawing Sheets

PREPARATION OF PHENOL VIA ONE-STEP HYDROXYLATION OF BENZENE CATALYZED BY COPPER-CONTAINING MOLECULAR SIEVE

BACKGROUND OF THE INVENTION

1. Field of the Invention

The invention relates to a novel one-step process for preparation of phenol by hydroxylation of benzene with hydrogen peroxide catalyzed by molecular sieves doped with copper ions. With proper solvent, a phenol yield of 15–35%, selectivity close to 100% and phenol/Cu TON around 100 could be achieved at a temperature lower than 80° C.

2. Description of the Prior Art

Phenol is an important compound for industry and pharmaceuticals. It can be used as a starting material as well as an intermediate for manufacture of many chemicals, such as dyes, bactericides and herbicides. Therefore, its demand has always been extremely great; its annual world production had been reached to $4.9 \times 10^6$ tons in 1996[K. Weissermel and H. J. Arpe, "Industrial Organic Chemistry", $3^{rd}$ ed., VCH Publishers, Inc., New York, N.Y., U.S.A. 1997, p. 347]. Although a direct oxidation process of benzene to phenol would be the most economical route, until now only the indirect manufacturing processes have been operated, that is, benzene was reacted at first into an intermediate which was then reacted into phenol. The reason resided in that the oxidation capability of phenol is higher than that of benzene and the selectivity of one-step oxidation of benzene into phenol is generally not high. In United State and Japan, the most popular process operated presently for phenol production is the cumene process [K. Weissermel and H. J. Arpe, supra, p. 347], which includes the catalytic alkylation of benzene to cumene and consequent oxidation of cumene to phenol and acetone. Acetone is generated in stoichiometric amount as the side product. The complication of this multi-step process as well as the cost of product separation leave the direct oxidation of benzene to phenol in a single step to be of great challenging to synthetic chemists.

In Europe, a two-step process was used predominantly [K. Weissermel and H. J. Arpe, supra, p. 347], wherein toluene as the starting material was subjected to a catalytic oxidation to form benzoic acid which was then decomposed catalytically into phenol and carbon dioxide. These processes were not, of course, as economic as the one-step oxidation of benzene into phenol.

Many approaches for one-step direct oxidation of benzene into phenol have been reported, yet little success has been achieved due to low phenol yield, expensive oxidants, and high operating cost. For example, a process using ZSM-5 zeolite as catalyst and $N_2O$ as oxidant has been well examined as an one-step reaction for oxidizing benzene into phenol (see, for example, V. I. Sobolve, A. S. Kharitonov, Y. A. Paukshtis and G. I. Panov, *J. Mol. Catal.*, 1993, 84, 117; R. Burch and C. Howitt, *Appl. Catal.*, 1992, 86, 139; J. S. Yoo, A. R. Sohail, S. S. Grimmer and J. Z. Shyu, *Appl. Catal., A: General* 1994, 117, 1). Its greatest disadvantage resided in that it should be operated at an elevated temperature of higher than 200° C. and $N_2O$ is an expensive oxidant which resulted in an undue high cost.

Another process whose reaction mechanism often been discussed is one using divalent iron as the catalyst and hydrogen peroxide as oxidant (Fenton's reaction) (J. R. Lindsay-Smith and R. O. C. Norman, *J. Chem. Soc.*, 1969, 2897). However in view of the catalytic efficiency, its phenol yield was extremely low, the turnover number (TON, or phenol yield per active site) was around 1, and that rendered it evidently of little developing potential.

Furthermore, liquid phase reactions using Ti- or V-containing zeolites as catalysts and hydrogen peroxide as oxidant have been reported (J. S. Reddy, S. Sivasanker and P. Ratnasamy, *J. Mol. Catal.*, 1992, 71, 373; A. V. Ramaswany, S. Sivasanker and P. Ratnasamy, *Micro. Mater.*, 1994, 2, 451), wherein some deep oxidation side products such as p-benzoquinone and hydroquinone were produced and the phenol selectivity was not high. The same reaction using tetra-nuclear platinum complex as a catalyst has been proposed (A. V. Ramaswany, S. Sivasanker and P. Ratnasamy, *Micro. Mater.*, 1994, 2 , 451), and the difficulty laid in the preparation of such a catalyst. Still another process using ammonium salt of mono-vanadium(V)-substituted hetero-polyamines as the catalyst has been tried (K. Sakai and K. Matsumoto, *J. Mol. Catal*, 1991, 67, 7), but a low phenol yield was obtained. Recently, an one-step process for oxidizing benzene into phenol was reported, wherein a mesoporous molecular sieve, MCM-41, either exchanged with copper ion or loaded with copper oxide was used as the catalyst, 10 atm of oxygen as oxidant, ascorbic acid as reducing agent and acetic acid as solvent (K. Nomiya, K. Yagishita, Y. Nemoto and T. Kamataki, *J. Mol. Catal. A,* 1997, 126, 43). Although it claimed to have a very high phenol selectivty, the use of ascorbic acid and acetic acid as well as the formation of di-ketones as side products could increase the difficulty in product separation. Furthermore, its phenol yield did not exceed 1.5%, and its phenol/Cu TON was not higher than 15. This report revealed also that hydrogen peroxide generated during the reaction was the true oxidant.

References

1. K. Weissermel and H.-J. Arpe, "Industrial Organic Chemistry", $3^{rd}$ ed., VCH Publishers, Inc., New York, N.Y., U.S.A. 1997, p. 347.
2. V. I. Sobolve, A. S. Kharitonov, Y. A. Paukshtis and G. I. Panov, *J.Mol.Catal.*, 1993, 84, 117
3. R. Burch and C. Howitt, *Appl.Catal.*, 1992, 86, 139
4. J. S. Yoo, A. R. Sohail, S. S. Grimmer and J. Z. Shyu, *Appl. Catal., A:general* 1994, 117, 1
5. J. R. Lindsay-Smith and R. O. C. Norman, *J. Chem. Soc.*, 1969, 2897
6. J. S. Reddy, S. Sivasanker and P. Ratnasamy., *J.Mol.Catal.*, 1992, 71 ,373
7. A. V. Ramaswany, S. Sivasanker and P. Ratnasamy., *Micro. Mater.*, 1994, 2, 451
8. K. Sakai and K. Matsumoto, *J.Mol.Catal*, 1991, 67, 7
9. K. Nomiya, K. Yagishita, Y. Nemoto and T. Kamataki, *J. Mol. Catal A,* 1997, 126, 43
10. J. Okamura, S. Nishiyama, S. Tsuruya and M. Masai, *J. Mol. Catal. A.*, 1998, 135, 133.

In addition, many related patents are described as follows:

(1) In relation to the process via acid-catalyzed decomposition of cumene hydroperoxide into phenol and acetone, a number of solid acid catalysts has been used instead of sulfuric acid which is used in the current industrial process for the acid-catalyzed decomposition. See, for example, U.S. Pat. Nos. 4,870,217 (1989), 4,898,987 (1990), 4,898,995 (1990), 4,209,465 (1980), 4,246,203 (1981), 4,267,379, 4,267,380 (1981), and 4,482,757 (1984); and JP Patent No. 54157531 (1979).

(2) Monsanto Company has developed in recent years a process for one-step oxidizing benzene into phenol by using $N_2O$ as oxidant and iron-containing zeolite as the catalyst at a reaction temperature of 225–600° C. Such a process was proposed mainly by the research group of Gennadii I. Panov in Russia. The related patents were as follows: U.S. Pat. Nos. 5,110,995 (1992), 5,672,777 (1997), 5,756,861 (1998), 4,559,314 (1985), 4,982,013, 5,001,280, 5,055,623, 5,077,026 (1991), 5,098,687, 5,110,995 (1992), and 5,367,099 (1994); JP Patent No. 06009464 (1994); RU Patent No. 2010790 (1994); GB Patent No. 2116974 (1983); and WO Patent Nos. 9500066, and 9500065 (1995).

(3) Since the catalytic ability of Ti-silicalite for the hydroxylation of aromatics was discovered, there have been many patents disclosed in applications of Ti- or V-containing molecular sieves to such reactions. See, for example, U.S. Pat. Nos. 5,783,167 (1998), 5,569,791 (1996), 5,246,689, 5,198,203, 5,196,633 (1993), 5,174,888, 5,102,643, 5,098,684 (1992), and 5,064,629 (1991); and WO Patent Nos. 9429022 (1994), 9302013 (1993), and 9118833 (1991).

(4) As a part of the multiple-step reaction using toluene as the starting material in the European process for production of phenol, the decarboxylative hydrolysis of chlorobenzoate salt was disclosed in U.S. Pat. No. 3,912,784 (1975), and the oxidative decarboxylation of arylcarboxylic acids or their salts, esters, and anhydrides, was disclosed in U.S. Pat. Nos. 4,405,823, 1983; and 5,210,331, 1993.

(5) Still other processes are as the following:
   (i) steam oxidation of cyclic or open-chain alkane to phenols, catalyzed by $ZnO/TiO_2$, $ZnO/V_2O_5$, $ZnO/TiO_2/La_2O_3$ and the like (U.S. Pat. No. 4,061,685, 1977).
   (ii) hydrolysis of iodobenzene in a liquid phase, catalyzed by cuprous salts such as $Cu_2O$, CuI, CuCl and the like (U.S. Pat. No. 4,684,749, 1987).

Among these mentioned processes, only those of (2) and (3) were one-step processes for oxidation of benzene into phenol. The Monsanto process using iron-containing ZSM zeolites as catalysts and $N_2O$ as oxidant has a greatest disadvantage as it must be carried, out at an elevated temperature of 225–600° C. and its production cost is greatly determined by the price of $N_2O$ oxidant at different production area thereof. On the other hand, the process involving liquid phase reactions using Ti- or V-containing zeolites as catalysts and hydrogen peroxide as oxidant may generate some deep oxidation side products such as hydroquinone and benzoquinone. This explains why Ti- or V-containing zeolites have been used as catalysts in industrial processes for manufacture of hydroquinone and catechol through hydroxylation of phenol but not for producing phenol.

Related Description of the Applications of Copper-Containing Molecular Sieves in Catalytic Reactions In the past decade, copper-containing molecular sieves has drawn great attention on its applications in decomposition of nitrogen monoxide. Such copper-containing molecular sieves were prepared by ion-exchange of molecular sieves with copper ions, wherein copper ions were not incorporated in the framework of the molecular sieves. Moreover, applications of such copper-containing molecular sieves in oxidation of benzene have not been disclosed heretofore.

Accordingly, there still needs a process for preparing phenol by oxidation of benzene with improved yield and as stated above, there has not been a process for producing phenol by one-step oxidation of benzene catalyzed by molecular sieves containing copper in the framework thereof.

SUMMARY OF THE INVENTION

The invention relates to a novel one-step process for preparation of phenol by hydroxylation of benzene with hydrogen peroxide catalyzed by molecular sieves doped with copper ions. With proper solvent, a phenol yield of 15–35%, selectivity close to 100% and phenol/Cu TON around 100 could be achieved at a temperature lower than 80° C.

BRIEF DESCRIPTION OF THE DRAWINGS

The invention, as well as its many advantages, may be further understood by the following detailed description and drawings in which.

DETAILED DESCRIPTION OF THE PREFERRED EMBODIMENT

Figure 1:
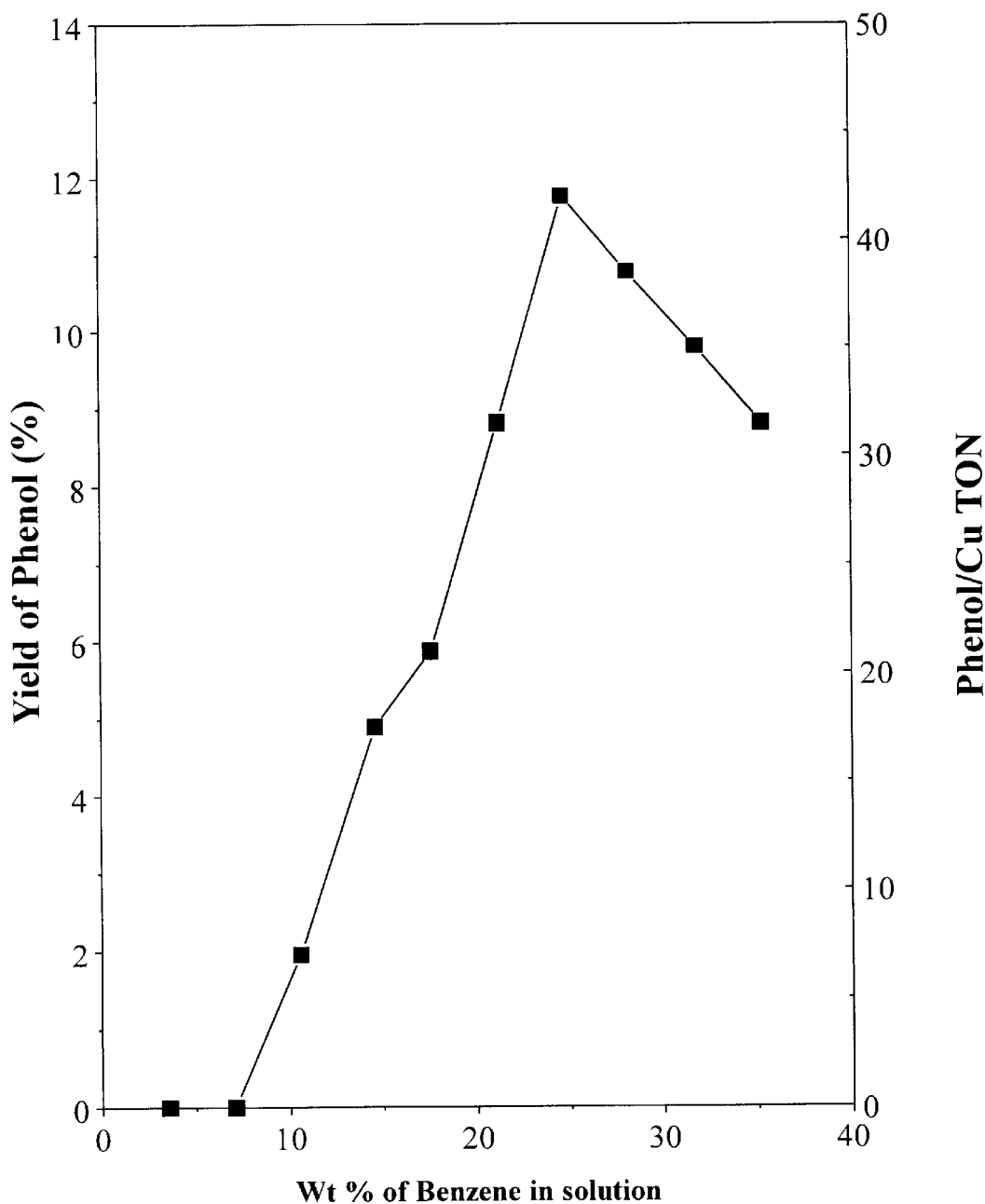
FIG. 1 is a plot showing the effect of benzene concentration on the phenol yield.

As stated above, the invention provides a novel one-step process for preparation of phenol by hydroxylation of benzene with hydrogen peroxide catalyzed by molecular sieves doped with copper ions, characterized in that with proper solvent and at a temperature lower than 80° C., a phenol yield of 15–35%, selectivity close to 100% and phenol/Cu TON around 100 could be achieved.

The copper-containing molecular sieves used in the process for one-step hydroxylation of benzene to phenol can be prepared by the process comprising the following steps:

(i) mixing aluminum salts or organo aluminum oxide with phosphorus-containing salts or acid compounds or organo-phosphorus compounds, or mixing solutions thereof, wherein the Al/P mole ratio is in the range of 0.5–1.5;

(ii) adding copper salts or its solutions in the reaction mixture of step (i), wherein the Cu/Al mole ratio is in the range of 0–0.5;

(iii) adding an organic template reagent in the reaction mixture of step (ii), wherein organic template reagent can be dipropylamine, triethylamine, or tripropylamine;

(iv) subjecting the reaction mixture of step (iii) to a hydrothermal reaction at 100–250° C.;

(v) separating solid precipitate from the reaction mixture of step (iv), washing with water and drying; and (vi) calcining the said solid of step (v) at a temperature lower than 650° C. to remove the organic template reagent.

Alternatively, the copper-containing molecular sieve used in the process for one-step hydroxylation of benzene to phenol can be prepared by the process comprising the following steps:

(i) mixing silicon salts or organo silicon oxide with aluminum salts or organo aluminum oxide compounds, or mixing the solutions thereof, wherein the Al/Si mole ratio is in the range of 0–0.5;

(ii) adding copper salts or its solution in the reaction mixture of step (i), wherein the Cu/Si mole ratio is in the range of 0–0.5;

(iii) adding an organic template reagent in the reaction mixture of step (ii), wherein said organic template reagent is tetraethyl-ammonium salts, tetrapropylammonium salts, or cetyltrimethyl-ammonium salts;

(iv) subjecting the reaction mixture of step (iii) to a hydrothermal reaction at 100–250° C.;

(v) separating solid precipitate from the reaction mixture of step (iv), washing with water and drying; and (vi) calcining the said solid of step (v) at a temperature lower than 650° C. to remove the organic template reagent.

In some embodiments according to the invention, several types of molecular sieves containing transition elements have been synthesized by the above-mentioned hydrothermal synthetic processes, including microporous molecular sieves with crystalline structures of ZSM-5 zeolite, $AlPO_4$-5 and VPl-5 aluminum phosphates, and mesoporous MCM-41 molecular sieve. It has been found that all copper-containing molecular sieves have catalytic activities for one-step oxidation of benzene to phenol, and in particular, $AlPO_4$-5 aluminum phosphate molecular sieve doped with copper has the most optimal activity.

The solvent used in the novel process for one-step hydroxylation of benzene to phenol according to the invention is preferably acetonitrile.

The oxidant used in the novel process for one-step hydroxylation of benzene to phenol according to the invention is preferably hydrogen peroxide.

The novel process for one-step hydroxylation of benzene to phenol according to the invention is performed in the temperature range of 30–80° C., and preferably at 60° C.

The novel process for one-step hydroxylation of benzene to phenol according to the invention is not restricted to benzene as the reactant. The novel process can be performed with toluene, xylene, trimethylbenzene, diethylbenzene, triethylbenzene, propylbenzene, butylbenzene and the like as the reactant, and preferably with benzene.

The novel process for one-step hydroxylation of benzene to phenol according to the invention can be carried out in a manner known to those skilled in the art of organic synthesis.

The invention will be further described in more detailed by the following non-limiting examples.

EXAMPLES

Example 1

Preparation of Aluminophosphate Molecular Sieves Doped with Copper Ions

To a 100-ml Erlenmeyer flask was charged in 5.5 g pseudo boehmite and 15 g water. In a separate small flask, 9.2 g phosphoric acid was mixed homogeneously with 10 g water. This homogeneous aqueous phosphoric acid solution was then added dropwise to the aluminum-containing material in the Erlenmeyer flask and stirred for half an hour. A desired amount of transition metal salts was dissolved in a minimum amount of water and then added slowly into the mixture in Erlenmeyer flask. After stirring for 3 hours, 4.2 g triethylamine was added and stirring was continued for another 3 hours. The content of the Erlenmeyer flask was then poured in a Teflon bottle which was then placed in a 316 stainless steel autoclave, and a hydrothermal reaction was carried out at 200° C. for 48 hours. Thereafter, the Teflon bottle was removed and cooled down in 5 minutes. The supernatant was decanted off and the precipitated solid was filtered off and washed several times with water. The product thus obtained was dried in an oven at 110° C. for 12 hours and finally, was calcined at 550° C. for 12 hours.

Example 2

Preparation of Copper-Containing ZSM-5 Zeolite 20 g Ludox aqueous silica gel suspension was added in a 100-ml Erlenmeyer flask and pH thereof was adjusted with dilute sulfuric acid to 3.5–4.5. In a separate flask, desired amount of copper sulfate was dissolved in a small amount of water. The copper sulfate solution was then added into the above mentioned Ludox aqueous silica gel suspension and mixed homogeneously. Tetrapropylammonium bromide (TPABr) as template agent was added and pH thereof was adjusted to 11. After stirring for 3 hours, the aqueous suspension was poured in a Teflon bottle that was then placed in a 316 stainless steel autoclave, and a hydrothermal reaction was carried out in an oven at 180° C. for 48 hours. Thereafter, the Teflon bottle was removed and cooled down in 5 minutes. The supernatant was decanted off and the precipitated solid was filtered off and washed several times with water. The product thus obtained was dried in an oven at 110° C. for 12 hours and finally, was calcined in a furnace at 550° C. for 12 hours.

Example 3

Characterization of Copper-Containing Molecular Sieves

X-ray powder diffraction patterns of the molecular sieves containing different copper contents thus-synthesized were compared with the JCPDS pattern library, and it was found that the crystalline phases of the so-obtained molecular sieves were nearly 100% pure. It is known that $AlPO_4$-5 aluminum phosphate molecular sieve is the most easily synthesized one among a variety of aluminum phosphate molecular sieves. There is great freedom in the synthetic conditions, such as the stirring time can vary from tens minutes to several days, and more than twenty kinds of organic compounds can be used as template reagent. In one embodiment of the invention, triethylamine was used as the template reagent. Moreover, a hydrothermal reaction time of longer than 24 hours and a temperature of higher than 160° C. was used to form readily the crystalline form of $AlPO_4$-5.

In addition to the confirmation that all the synthesized samples with different copper contents (0.5%, 1%, 2%) were $AlPO_4$-5 structures with good crystallinity, XRD patterns were also used to calculate the lattice parameter and the change of unit cell volume (Table 1). Since $AlPO_4$-5 belongs to hexagonal system, a and b axes have equal length. A step scan fashion was adopted during pattern scanning, wherein, lattice parameters were calculated based on 12 diffraction peaks having the strongest intensity and lattice parameters such as a, b, and c were obtained by inputting (h, k, l) values. From the relationship between doping amounts of Cu ions and values of lattice parameters, it could be seen that the unit cell volume increased with increase in the content of divalent copper ions. This meant that copper ions were incorporated in the framework of the aluminum phosphate other than in pores beyond such framework.

TABLE 1

Lattice parameters of different Cu-loading $AlPO_4$-5.

| Sample | a, b (Å) | c (Å) | Unit cell volume (Å$^3$) |
| --- | --- | --- | --- |
| $AlPO_4$-5 | 13.614 (0.004) | 8.484 (0.005) | 1362 |
| 0.5% CuAPO-5 | 13.637 (0.002) | 8.491 (0.002) | 1367 |
| 1% CuAPO-5 | 13.681 (0.013) | 8.445 (0.014) | 1369 |
| 2% CuAPO-5 | 13.654 (0.005) | 8.486 (0.005) | 1370 |

The appearance of crystal form of typical $AlPO_4$-5 is hexagonal prism and the height of its prism is much greater than its hexagonal plane. In general, the grains with hexagonal prism form tend to align into a spheroid or ellipsoidal shape. It was found from the scanning electron microphotographs that as the copper content increased the regularity of crystal alignment became worse. Some loose and discrete particulates appeared gradually while their crystal form of basic hexagonal prism changed into flat cylindrical. In view of the macroscopic crystal form revealed from SEM, it was suggested that when there were foreign metal atoms incorporated within the framework, the lattice would have distortion along the propagating direction of crystal growth.

In order to confirm the molecular sieve structure of samples thus-synthesized, $AlPO_4$-5 samples with different copper loadings were subjected to vibrational spectroscopy. The absorptions around 1100 and 730 $cm^{-1}$ were attributed to the internal symmetry stretching vibration of $AlO_4$ and $PO_4$ tetrahedron within the $AlPO_4$ framework. The absorption around 1230 $cm^{-1}$ was the external asymmetry stretching vibration of the $AlO_4$ and $PO_4$ tetrahedron, and absorptions around 630 $cm^{-1}$ and 560 $cm^{-1}$ were vibrations of double-four-membered rings or double-six-membered rings on the framework of the molecular sieve. Basically, no effect of copper substitution on the spectra could be observed and this meant that infrared absorption peaks confirmed definitely the molecular sieve structure of the catalysts synthesized above.

General Process of Catalytic Reaction in Liquid Phase

To 2 g catalyst in a three-necked flask was added a reaction solution containing 10 g reactants (mole ratio of reactant to solvent=1:5) and stirred under a reflux device. After heating to a temperature of 30–80° C., two equivalent of hydrogen peroxide (35%) was added and continued stirring for 3 hours. Products thus obtained were analyzed by GC-FID. In a blank catalytic reaction, the catalyst was omitted. The benzene conversion and phenol yield were calculated based on an external-standard toluene.

Example 4

Oxidation Reaction of Benzene Catalyzed with Various Catalysts Containing Copper In experiments of direct oxidation of benzene to phenol, various catalysts have been tried, however only the molecular sieves containing copper as those prepared in Examples 1 and 2 were active. Moreover, $AlPO_4$-5 incorporated with copper ion had optimal activity. By selecting suitable reaction conditions, product containing predominantly phenol could be obtained with a selectivity higher than 99.5%. Secondary oxidation products such as catechol, hydroquinone and p-benzoquinone, could only be detected at extremely trace amount with extremely low yield. Concurrently, $CuO/AlPO_4$-5 molecular sieves prepared by impregnation method as well as CuO and $Cu_2O$ were tested as catalyst in this reaction. In these cases, products therefrom contained mainly polymer of high molecular weight with low yield of phenol. This confirmed that active sites on the copper-containing molecular sieves should not be the extra-framework copper oxide. Table 2 shows catalytic activities of different types of copper-containing catalyst, error estimated on conversion was approximately ±1%.

TABLE 2

Benzene oxidation catalyzed by different Cu-containing catalysts.

| Catalyst | Conversion (%) | Phenol yield (%) |
| --- | --- | --- |
| 1% Cu-APO-5 | 28 | 28 |
| 1% CuO/AlPO$_4$ (imprenated) | 54 | 9 |

TABLE 2-continued

Benzene oxidation catalyzed by different Cu-containing catalysts.

| Catalyst | Conversion (%) | Phenol yield (%) |
| --- | --- | --- |
| 1% Cu-APO-5 (used)[a] | 18 | 18 |
| CuO | 78 | 8 |
| Cu$_2$O | 66 | 4 |

Reaction conditions: 60° C., acetonitrile as the solvent.
[a] the used sample was calcined at 550° C. for 8 hours.

Example 5

Oxidation of Benzene in Water Catalyzed with Different Mount of $Cu(NO_3)_2 \cdot 3H_2O$ Catalyst In order to verify whether the active center was free divalent copper ion possible existing in the reaction solution, aqueous copper nitrate solutions in different amounts were used as catalysts. Table 3 shows the result of this experiment. It can be seen that the catalytic activity of copper nitrate was much lower than that of Cu-APO-5. This suggests that free divalent copper ion is not the main active center.

TABLE 3

Benzene oxidation with different amount of $Cu(NO_3)_2 \cdot 3H_2O$ in water as catalyst.

| Catalyst weight (g) | Conversion (%) | Phenol yield (%) |
| --- | --- | --- |
| 8 × 10$^{-3}$ | 13 | 6 |
| 4 × 10$^{-3}$ | 6 | 4 |
| 2 × 10$^{-3}$ | 2 | 2 |
| 1 × 10$^{-3}$ | 1 | 1 |

Reaction conditions: 60° C., 3 hours; benzene: acetonitrile: $H_2O_2$ = 1.0 g: 2.3 g: 2.5 ml.

Example 6

Benzene Oxidation Catalyzed by Different Amount of 1% Cu-APO-5

In order to observe the effect of different amount of catalyst on the phenol yield, the amount of catalyst was varied in the reaction. Table 4 shows the result of this experiment. It could be seen that a linear increase in phenol yield was obtained when the catalyst amount increased. Hence, it suggests that the rate-determining step of benzene oxidation is not diffusion but is determined by the true chemical reaction. On the other hand, when amount of catalyst used in this example was up to 0.3 g, in addition to the main phenol product, yield of secondary products such as catechol, hydroquinone and other high molecular weight side-products might increase significantly. This suggests that as phenol concentration in the solution was higher than a certain value, phenol would compete with benzene in the oxidation reaction.

TABLE 4

Benzene oxidation with different amount of 1% Cu-APO-5.

| catalyst weight (g) | conversion (%) | Phenol yield (%) |
|---|---|---|
| 0.1 | 17 | 17 |
| 0.2 | 28 | 28 |
| 0.3 | 46 | 35 |

Reaction conditions: 60° C., 3 hours;
benzene: acetonitrile: $H_2O_2$ = 1.0 g: 2.3 g: 2.5 ml.

Example 7

Benzene Oxidation with Different Cu-Loading AlPO$_4$-5

Table 5 shows the result of benzene oxidation catalyzed with different Cu-loading AlPO$_4$-5. AlPO$_4$-5 with zero Cu-loading was completely inactive. This demonstrated that copper ion is indeed the active center with respect to benzene oxidation. The catalytic activity of %Cu-APO-5 was significantly better than that of 0.5%Cu-APO-5, since increasing copper loading means increasing the number of active sites. On the other hand, phenol yields were about the same when 1%Cu-APO-5 and 2%Cu-APO-5 were used as catalysts, and, furthermore, in case of using 2%CuAPO-5 as catalyst, a small amount of macromolecule products were produced in the reaction solution. This was similar to the situation when CuO was used as catalyst and meant that in case of 2%Cu-APO-5, a part of copper ion outside the framework might be in a form of metal oxide. Whereas in case of low Cu-loading, such as 0.5%Cu-APO-5 and 1%Cu-APO-5, copper ions should be within the framework of the molecular sieve.

TABLE 5

Benzene oxidation with different Cu-loading AlPO$_4$-5.

| catalyst | Conversion (%) | Phenol yield (%) |
|---|---|---|
| APO-5 | 0 | 0 |
| 0.5% CuAPO-5 | 12 | 12 |
| 1% CuAPO-5 | 28 | 28 |
| 2% CuAPO-5 | 45 | 29 |

Reaction conditions: 60° C.

Example 8

Effect of Solvent on Benzene Oxidation

In an attempt to examine the effect of solvent on benzene oxidation, a variety of solvent including acetone, dimethyl sulfoxide, acetonitrile, acetic acid, and N,N-dimethylformamide were used. The result was shown in Table 6. It is found that acetonitrile was the only active one. This suggested that acetonitrile plays a very important role in stabilizing the active center or the intermediate products.

TABLE 6

Effect of solvent on benzene oxidation.

| solvent | conversion (%) | phenol/Cu TON |
|---|---|---|
| DMSO | 0 | 0 |
| DMF | 0 | 0 |
| Acetone | 0 | 0 |
| Acetonitrile | 28 | 98 |
| Acetic acid | 0 | 0 |

Reaction conditions: 60° C., 3 hours; 1% CuAPO-5 as catalyst.

Example 9

Effect of Temperature on Benzene Oxidation

Table 7 shows activity data of benzene oxidation at different temperatures. A reaction temperature of 60–70° C. gave the highest phenol yield. As the temperature approaching 80° C., which was close to the boiling point of benzene, it caused a considerable consumption of benzene due to evaporation at this temperature. Hence, 60–70° C. is the most optimal reaction temperature.

TABLE 7

Effect of temperature on benzene oxidation.

| Temperature (° C.) | Conversion (%) | Phenol yield (%) |
|---|---|---|
| 25 | 0 | 0 |
| 40 | 16 | 16 |
| 50 | 24 | 24 |
| 60 | 28 | 28 |
| 70 | 30 | 30 |
| 80 | 88 | 2 |

Reaction conditions: 60° C., 1% CuAPO-5 as the catalyst.

Example 10

Effect of Reactant Concentrations on Benzene Oxidation

In attempt to know if adsoption of benzene ring on the surface of the molecular sieve were involved in the reaction, the initial concentration of benzene was varied. In case that the activity changes linearly with benzene concentration, it indicates that benzene reacts homogeneously in solution and is not limited by the step of adsorption on the catalyst surface. On the other hand, if the activity approaches a plateau or lowers as the benzene concentration increases to a certain extent, it should indicate that benzene reacts through adsorbing on the surface of the molecular sieve and thereby is limited by the amount of adsorption. Results in FIG. 1 reveals that the reaction cannot occur at a benzene concentration lower than 7%. Beyond 7% phenol yield changes almost linearly with benzene concentration, and phenol yield reachs an optimal value at a benzene concentration of 25%. Above 25%, phenol yield decreases with benzene concentration. Thus, it implies that adsorption of benzene ring on the active site over the surface of the catalyst must be involved in the reaction process.

Figure 2:
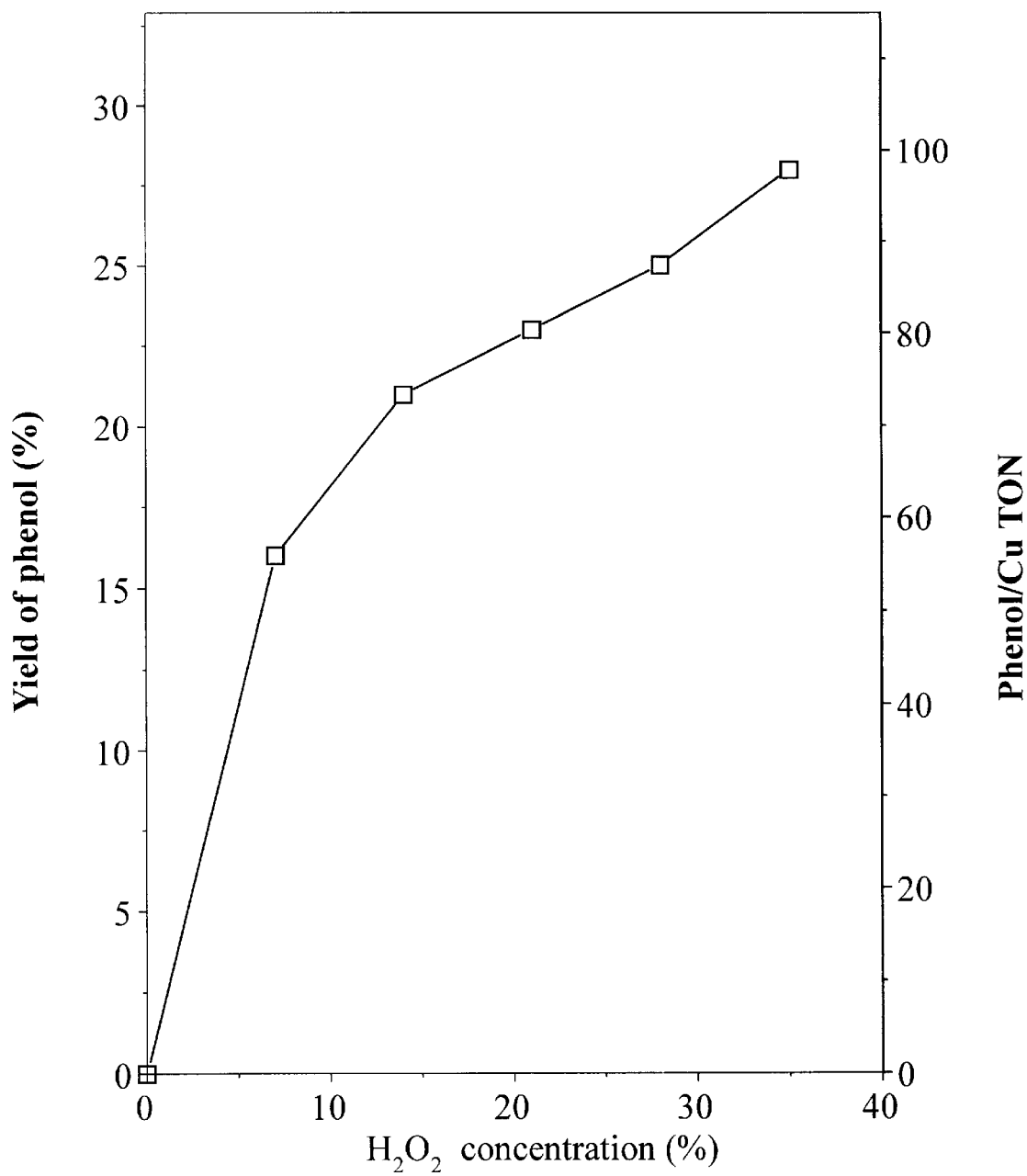
FIG. 2 is a plot showing the effect of $H_2O_2$ concentration on the phenol yield.

An experiment by changing the concentration of hydrogen peroxide was also performed and its result was shown in FIG. 2. As the concentration of hydrogen peroxide increases, the activity becomes better but not in a linear relationship and the curve approaches a plateau gradually.

Therefore, it is believed that hydrogen peroxide, like benzene, has to adsorb on the surface active sites. The results also imply that the adsorption capability of benzene on the active sites is probably stronger than that of hydrogen peroxide. At a benzene concentration above 25%, benzene would displace hydrogen peroxide originally adsorbed on the active site so as to cause a decrease in the reactivity.

Example 11

Effect of Alkyl-Substituted Benzene Rings as Reactants on Oxidation Reaction

Figure 3:
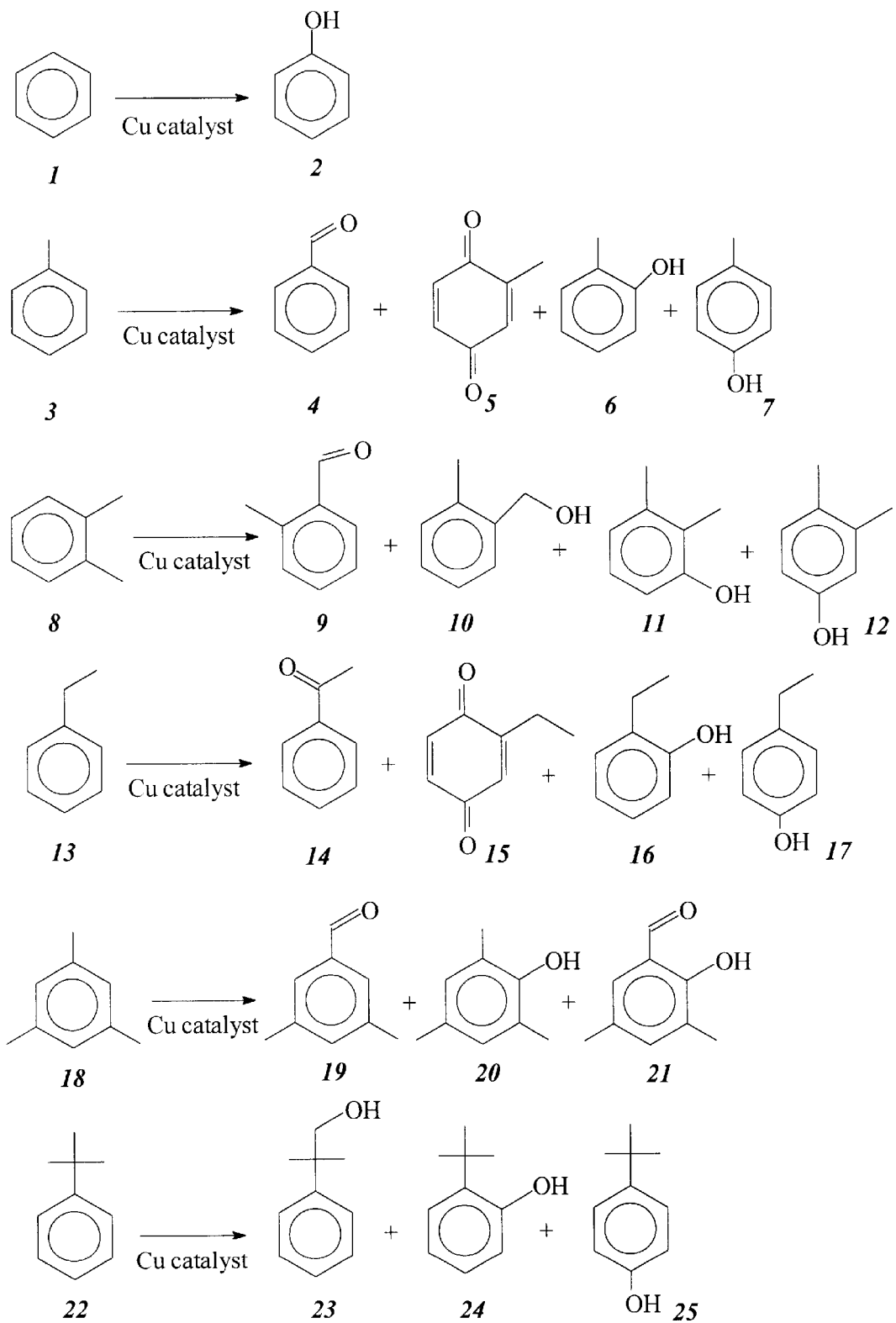
FIG. 3 is a plot showing the products obtained in oxidation of various alkyl-substituted aromatic reactants using molecular sieves doped with copper ions as catalysts.

The invention concerning one-step hydroxylation of benzene for preparing phenol catalyzed by molecular sieves doped with copper ions is not limited to benzene as the reactant. Various alkyl-substituted benzene rings could also be subjects as the reactants. FIG. 3 reveals the products formed by using various alkyl-substituted benzene rings as reactants. The conversion and product yield are tabulated in Table 8. Therein the products can be divided into two groups: one group includes phenols and quinones which are the products of hydroxylation of the benzene ring, and the other includes alcohols and aldehydes which are the products of oxidation of the alkyl chains. In oxidation reactions involving OH radical, the α-carbon of the alkyl group substituted on benzene ring is generally the most active position subjected to oxidation. However, the reaction data shown in this example is just contrary. It shows that the oxidation reaction in this invention is not a simple oxidation reaction with OH radicals, instead during the reaction benzene ring should be adsorbed on the active sites of catalyst surface. Therefore, the product yield decreases markedly as the reactant becomes bulky and with great steric hindrance.

TABLE 8

Results of oxidation of alkyl-substituted benzene rings.

| Reactant | Product yield (%) | | | | Conversion (%) |
|---|---|---|---|---|---|
| Benzene (1) | 2 | | | | |
|  | 28 | | | | 28 |
| Toluene (3) | 4 | 5 | 6 | 7 | |
|  | 3.8 | 0.6 | 7.0 | 2.5 | 14 |
| 1,2-Dimethylbenzene (8) | 9 | 10 | 11 | 12 | |
|  | 3.8 | 0.6 | 2 | 2.2 | 8.9 |
| Ethylbenzene (13) | 14 | 15 | 16 | 17 | |
|  | 4.6 | 0.6 | 2.6 | 1.8 | 9.6 |
| 1,3,5-Trimethylbenzene (18) | 19 | 20 | 21 | | |
|  | 4.6 | 1.2 | 1 | | 6.7 |
| Isobutylbenzene (22) | 23 | 24 | 25 | | |
|  | 0.3 | 0.3 | 1.2 | | 1.8 |

Reaction condition: 60°0 C., 1% CuAPO-5 as catalyst.
The reactants and products are labled in Arabic figures and the structural formulas are shown in FIGURE 3.

Many changes and modifications in the above-described embodiments of the invention can, of course, be carried out without departing from the scope thereof. Accordingly, to promote the progress in science and the useful arts, the invention is disclosed and is intended to be limited only by the scope of the appended claims.

What is claimed is:

1. A one-step process for preparing phenol from benezene or alkyl-substituted benzene comprising reacting benzene or an alkyl-substituted benzene with hydrogen peroxide in a solvent at a temperature lower than 150° C. in the presence of a catalyst comprising a molecular sieve containing copper ions.

2. An one-step process for preparing phenols as claimed in claim 1, wherein an alkyl-substituted benzene ring, is reacted with the hydrogen peroxide.

3. An one-step process for preparing phenols as claimed in claim 1, wherein the catalyst is selected from the group consisting of copper containing aluminophosphate molecular sieves of the crystalline structure of $AlPO_4$-5, $AlPO_4$-8, $AlPO_4$-11, $AlPO_4$-31, SAPO-37, VPl-5; and copper containing zeolites of the crystalline structure of ZSM-5, ZSM-11, zeolite-Y, zeolite-X, zeolite-A, β-zeolite; and mesoporous molecular sieves of MCM-41, and MCM-48 structures.

4. An one-step process for preparing phenols as claimed in claim 1, wherein the molecular sieve is doped with copper ions and contains copper ions incorporated in the framework of said molecular sieve.

5. An one-step process for preparing phenols as claimed in claim 1, wherein the copper content in the molecular sieve ranges from 0.1 to 10 weight percent.

6. An one-step process for preparing phenols as claimed in claim 1, wherein the concentration of said benzene or alkylbenzene ranges from 5–60%.

7. An one-step process for preparing phenols as claimed in claim 1, wherein the $H_2O_2$ concentration ranges from 1–70%.

8. An one-step process for preparing phenols as claimed in claim 1, wherein the solvent is acetonitrile.

9. An one-step process for preparing phenol as claimed in claim 1, wherein said reaction temperature is in the range of 30–80° C.

10. An one-step process for preparing phenols as claimed in claim 2, wherein the reaction temperature is in the range of 30–150° C.

11. A one-step process for preparing phenols as claimed in claim 2, wherein the catalyst is selected from the group consisting of copper containing aluminophosphate molecular sieves of the crystalline structure of $AlPO_4$-5, $AlPO_4$-8, $AlPO_4$-11, $AlPO_4$-31, SAPO-37, VPl-5; and copper containing zeolites of the crystalline structure of ZSM-5, ZSM-11, zeolite-Y, zeolite-X, zeolite-A, β-zeolite; and mesoporous molecular sieves of MCM-41, and MCM48 structures.

12. A one-step process for preparing phenols as claimed in claim 2, wherein the molecular sieve is doped with copper ions and contains copper ions incorporated in the framework of said molecular sieve.

13. A one-step process for preparing phenols as claimed in claim 3, wherein the molecular sieve is doped with copper ions and contains copper ions incorporated in the framework of said molecular sieve.

14. A one-step process for preparing phenols as claimed in claim 2, wherein the copper content in the molecular sieve ranges from 0.1 to 10 weight percent.

15. A one-step process for preparing phenols as claimed in claim 3, wherein the copper content in the molecular sieve ranges from 0.1 to 10 weight percent.

16. A one-step process for preparing phenols as claimed in claim 2, wherein the concentration of said benzene or alkylbenzene ranges from 5–60%.

17. A one-step process for preparing phenols as claimed in claim 2, wherein the $H_2O_2$ concentration ranges from 1–70%.

18. A one-step process for preparing phenols as claimed in claim 2, wherein the solvent is acetonitrile.

* * * * *